(12) United States Patent
Lin

(10) Patent No.: US 6,520,004 B1
(45) Date of Patent: Feb. 18, 2003

(54) TEST APPARATUS AND METHOD OF MEASURING MAR RESISTANCE OF FILM OR COATING

(75) Inventor: Li Lin, Wallingford, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/601,664
(22) PCT Filed: Mar. 10, 1999
(86) PCT No.: PCT/US99/05226
§ 371 (c)(1),
(2), (4) Date: Aug. 3, 2000
(87) PCT Pub. No.: WO99/46576
PCT Pub. Date: Sep. 16, 1999

Related U.S. Application Data

(60) Provisional application No. 60/077,518, filed on Mar. 11, 1998.

(51) Int. Cl.⁷ .................................. G01N 3/46
(52) U.S. Cl. .................................. 73/81; 73/7
(58) Field of Search .......................... 73/81, 78, 82, 73/83, 7, 150 R, 105, 1.89

(56) References Cited

U.S. PATENT DOCUMENTS

| | | | | |
|---|---|---|---|---|
| 2,564,519 A | * | 8/1951 | Bergsman | 73/81 |
| 2,713,259 A | * | 7/1955 | Grodzinski et al. | 73/81 |
| 3,785,198 A | * | 1/1974 | Heetman | 73/78 |
| 4,848,141 A | * | 7/1989 | Oliver et al. | 73/81 |
| 4,856,326 A | * | 8/1989 | Tsukamoto | 73/799 X |
| 4,984,453 A | * | 1/1991 | Enomoto | 73/81 |
| 5,344,551 A | * | 9/1994 | Tsai et al. | 205/110 |
| 5,359,879 A | * | 11/1994 | Oliver et al. | 73/81 X |
| 5,517,860 A | | 5/1996 | Lin et al. | 73/78.9 |
| 5,546,797 A | * | 8/1996 | Dutta et al. | 73/81 X |
| 5,661,235 A | * | 8/1997 | Bonin | 73/105 |
| 5,866,807 A | * | 2/1999 | Elings et al. | 73/81 X |
| 5,994,010 A | * | 11/1999 | Tanaka et al. | 430/56 |
| 6,000,284 A | * | 12/1999 | Shin et al. | 73/7 X |

FOREIGN PATENT DOCUMENTS

| | | | | |
|---|---|---|---|---|
| CA | 2149228 | * | 4/1994 | G01N/3/46 |
| DE | 19618000 C1 | * | 8/1997 | G01N/3/46 |
| GB | 2146129 A | * | 4/1985 | |
| JP | 62-32340 | * | 2/1987 | 73/82 |
| JP | 62-245131 | * | 10/1987 | 73/78 |
| JP | 43742 | * | 2/1989 | 73/82 |
| WO | WO 96/10737 | * | 4/1996 | G01N/3/46 |

OTHER PUBLICATIONS

TDB–Acc–No.: NN85122975, IBM Technical Disclosure Bulletin vol. 28, No. 7, pp. 2975–2976, "Instrument for Testing Thin Films Such as Magnetic Tape", Dec. 1985.*

(List continued on next page.)

Primary Examiner—Thomas P. Noland
(74) Attorney, Agent, or Firm—Sudhir G. Deshmukh

(57) ABSTRACT

This invention concerns a test apparatus and procedure used for quantitative and qualitative characterization of scratch and mar behavior of films or coatings, more particularly automotive coatings. The apparatus includes a micro-indentor that penetrates and scratches the coating to be characterized together with interrelated components for measuring the force applied, the length and depth of the indentor penetration, the geometry of the disturbed coating surface as well as a system for measuring, analyzing and comparing test results.

32 Claims, 11 Drawing Sheets

OTHER PUBLICATIONS

Derwent–Acc–No.: 1993–007895 Abstract of SU 1714443 A1 "Spectrometric Test Instrument—Has Support to Compensate Vertical Component of Scratching Force and Torque" Lyasho et al, Feb. 1992.*

Derwent–Acc–No.: 1996–299189 Abstract of RU 2049326 C1 Hardness Meter—Has Pivoted Sprung Indentor Fixed Along Axis of Pendulum and Uses Force Meters to Measure Tangential and Perpendicular Forces Acting on Sample From Indentor, Beloseuich et al, Nov. 1995.*

Derwent–Acc–No.: 1980–D1279C Abstract of SU 676908 A "Materials Scratch Hardness Test Meter—" Berdinskik et al, Aug. 1979.*

Betz et al., Scratch Resistant Clear Coats: Development of New Testing Methods for Improved Coatings, Progress in Organic Coatings, 22 (1993) 27–37 Month Not Given.

Wu, Microscratch and Load Relaxation Tests for Ultra–Thin Films, J. Mater. Res., vol. 6, No. 2, Feb. 1991, 407–426.

* cited by examiner

TEST APPARATUS AND METHOD OF MEASURING MAR RESISTANCE OF FILM OR COATING

This application is a 35 U.S.C. §371 of PCT/US99/05226 filed on Mar. 10, 1999, which claims the benefit of U.S. Provisional No. 60/077,518 filed on Mar. 11, 1998.

BACKGROUND OF THE INVENTION

The present invention is generally directed to testing the mechanical properties of films and coatings, and more particularly directed testing scratch and mar resistance of coatings and to a testing apparatus used therein.

In principle, marring process can be caused by contact of a coated surface with a moving solid body, which induces stresses in the coated surface. One example of the marring process can be seen in coatings on automotive bodies, which are typically exposed to damage by abrasive elements, such as dust, dirt, surface scuffing during a car wash and weathering action. The marring of the coated surface results in loss of its esthetic appearance. The scratching or marring of a coated surface is especially undesirable in pigmented or clear coatings having high gloss. The scratch and mar resistance of a coating depends upon the physical properties, such as yield stress, toughness, Young's modulus and hardness of the coating composition. The foregoing physical properties are greatly affected by the properties, such as glass transition temperature, and chemical structure of the polymers included in the coating compositions. Thus, the measurement of scratch and mar resistance of a coating becomes very important in selecting the components, such as polymers, used in coating compositions. For example, by comparing the mar resistance of a coating composition containing one type of polymer against that containing a different polymer may be used to decide which polymer is better suited for providing a coating with optimal long term gloss and other physical properties.

One approach provides for rubbing a sand paper of a well defined structure in a prescribed fashion against a coated surface for inducing damage on the coated surface. Multiple contact points on the sand particles of the sand paper induce the damage, which is then visually quantified, typically on a scale of 0 to 10, wherein the number 10 represents no damage and 0 represents total damage. Alternatively, the damage induced on one coating is visually compared against the damage on a coating from a different coating composition under the same test conditions to determine which coating has lesser damage. Nonetheless, due to the subjective nature of any visual observation, which tends to vary from person to person, the foregoing tests are not sufficiently objective. Furthermore, the sand papers, though standardized, tend to have different grain structures, which can greatly affect the damage produced on the coating. It is also very difficult to quantitatively measure the damage produced by the multiple contact points of the sand particles on the sand paper. Additionally, digital pressure applied by tester during the prescribed rubbing action tends to vary. As a result, the damage resulting therefrom also tends to vary from one tester to the next. Thus, a need exists for a mar resistance testing apparatus that is less subjective and is more reproducible than the subjective non-reproducible testing procedures currently in use.

One apparatus in the literature is described by Wu in J. Mater. Res., Vol. 6, No. 2, pages 407 to 426, February 1991 (Materials Research Society). The apparatus defined in that article is not sufficiently robust for reproducible measurements on a large variety of coated substrates under conditions of high throughput.

SUMMARY OF THE INVENTION

The present invention is directed to an apparatus for measuring mar resistance of a test sample comprising:

means for indentor guiding, said means being mounted on a post of said apparatus comprise:

means for indentor driving having an indentor positioned therein, and means for sensing travel of said indentor towards and away from the surface of said test sample; and means for directing test sample, said means being positioned on a base of said apparatus comprise:

holder means to secure said test sample thereon with the surface of said test sample in perpendicular relationship with said indentor, and staging means for traversing said test sample in a direction tangential to said indentor, such that when a tip of said indentor is simultaneously driven into said test sample, a scratch a produced on the surface of said film or surface.

The present invention is also directed to a method of measuring mar resistance of a test sample comprising;

securing said test sample in staging means of an apparatus;

positioning an indentor in a perpendicular relationship to the exposed surface of said test sample, such that a tip of said indentor is in contact with said surface of said test sample;

driving said tip of said indentor into the surface of said test sample at a set rate while simultaneously traversing said test sample in a direction tangential to said indentor at a set speed in a set direction for scratching said surface of said test sample to produce a scratch thereon.

DETAILED DESCRIPTION OF THE PREFERRED EMBODIMENT

As used herein:

"Film" means a substantially planar free standing layer, such as a polyester film or sheet.

"Coating" means an adherent layer of a coating composition applied over a substrate surface.

Figure 1:
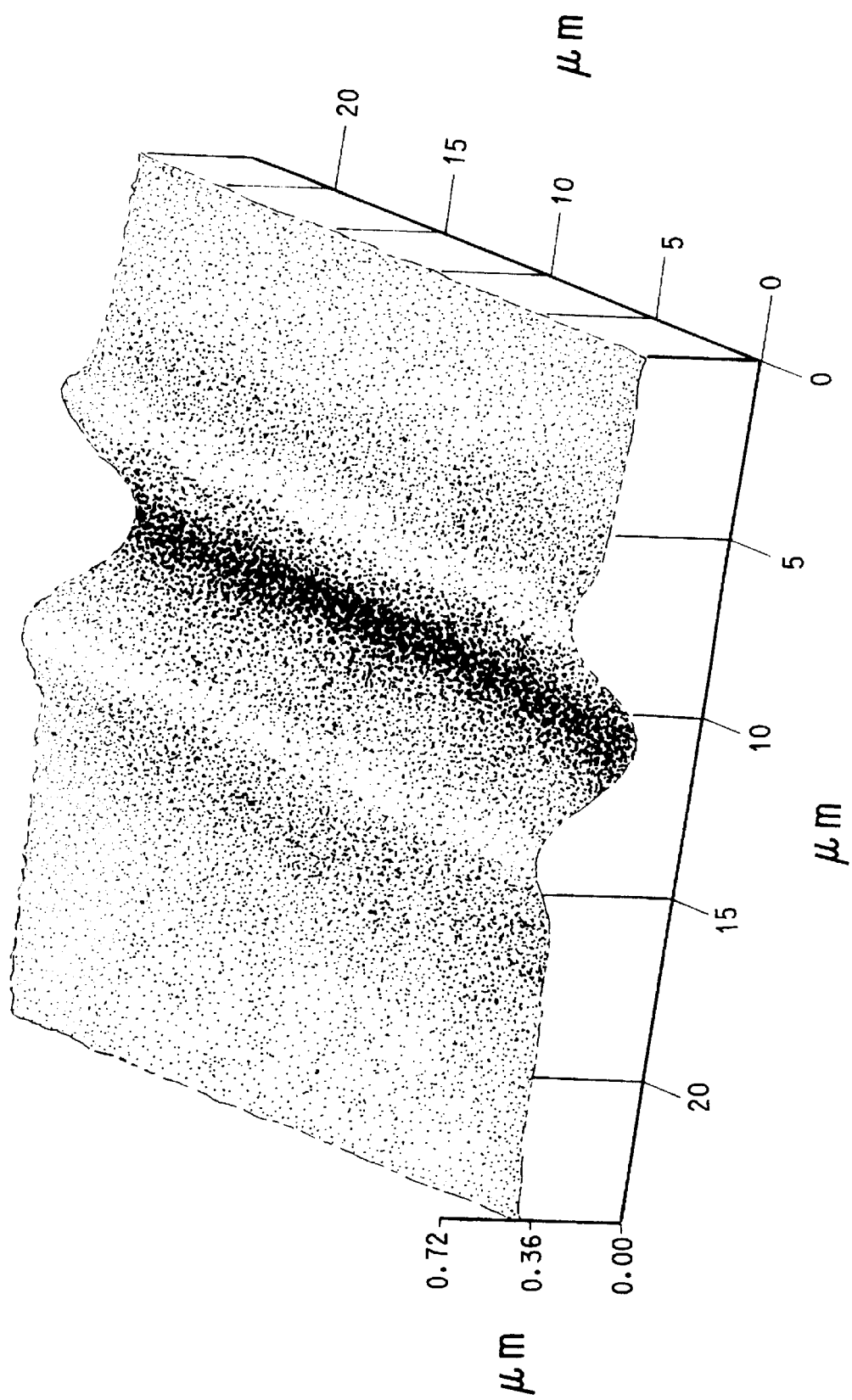
FIG. 1 is a rendition of a 3-dimensional atomic force microphotograph (AFM) of a micro-scratch produced during visco-plastic deformation of a film or coating.
Figure 2:
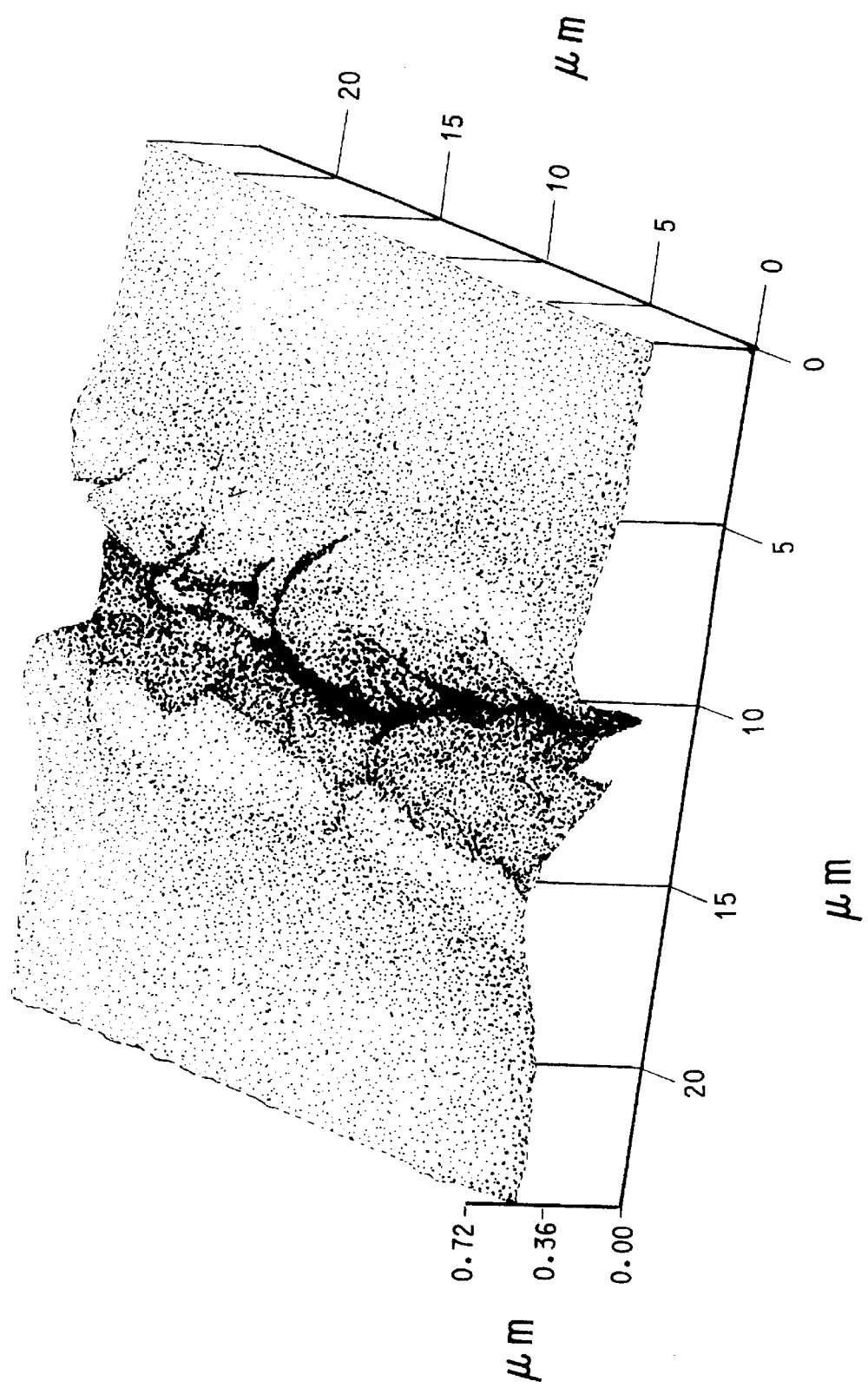
FIG. 2 is a rendition of a 3-dimensional ARM of a micro-scratch produced during fractured deformation of a film or coating.

The apparatus and method of this invention are directed to measuring mar and scratch resistance of a film or coating. The apparatus produces a micro-scratch on a coated test surface that closely mimics the scratch and mar damage typically observed on film or coated surfaces. The phenomenon of the scratch and mar damage is complex and applicant has determined that a typical micro-track or furrow left on a coated surface during the scratch and mar damage has two distinct elements. The mar damage, as seen in FIG. 1, may be in the form of a substantially smooth track produced during the visco-plastic deformation of the film or coating, or, as seen in FIG. 2, it may be in the form of a fissured track produced during the fractured deformation of the film or coating. The visual effect of these two distinct types of damages on viewer is significantly different. Applicant has discovered that the damage shown in FIG. 1 is more noticeable to trained experts than to a layman, whereas the damage shown in FIG. 2 is noticeable, to even a layman who is not trained to look for such defects. Thus, the present invention provides a more objective test capable of inducing these damages on a coating under predetermined reproducible conditions.

The present invention generally provides for a testing apparatus having means for deforming, i.e. micro-scratching, a test surface, capturing deformation information on the test surface in visual and graphic form, and analyzing the scratch damage.

Figure 3:
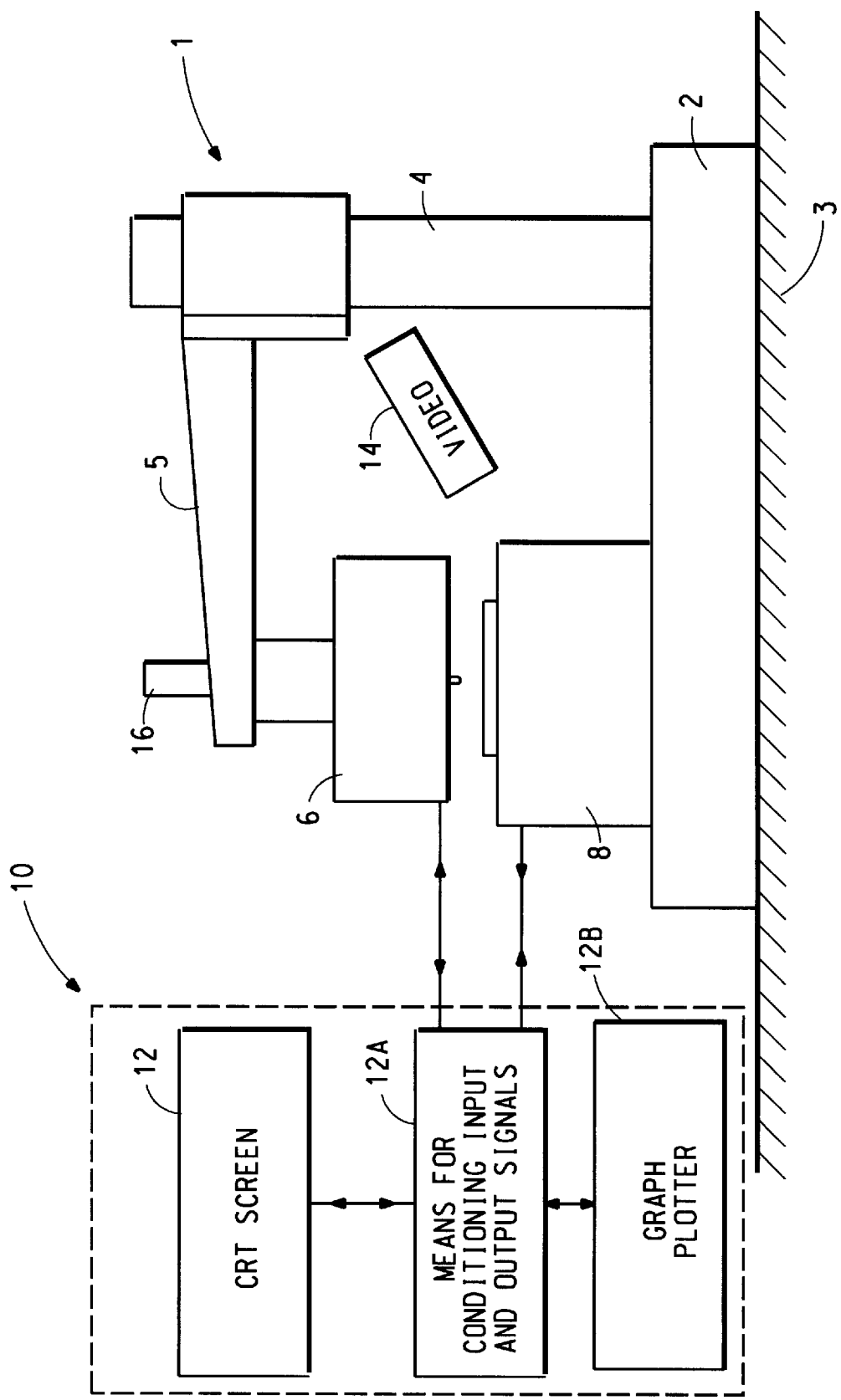
FIG. 3 is a schematic layout of various components of an apparatus of the present invention.

The schematics in FIG. 3 provide the various components of test apparatus 1 of the present invention. Test apparatus 1 includes a base 2 positioned on a platform 3 substantially isolated from vibrations to substantially prevent transmission of vibrations to apparatus 1. Conventional dampening means, such as air shock absorbers (not shown) are well suited for supporting platform 3. One exemplar of dampening means is Research Series Table Top Model No. RS4000-48-12 supplied by Newport Corporation, Irvine, Calif. Base 2 is provided with a post 4 having an arm 5 mounted thereon. Arm 5 is preferably adjustable, such that arm 5 can be positioned up or down on post 4. Means for indentor guiding 6 are fastened to arm 5. Means for directing test sample 8 are positioned on base 2. Apparatus 1 further includes conventional computer means 10, such as an IBM-compatible computer running on Windows® NT operating system, which is available from Microsoft Corporation of Redmond, Wash. Computer means 10 include means 12A for conditioning input and output signals to and from means for indentor guiding 6 and means for directing test sample 8 for controlling motions of an indentor 32 positioned on means for indentor guiding 6 and a test sample 56 (shown in FIGS. 6 and 8), which may be in the form of a film or a coating applied over a substrate. The motions of indentor 32 and test sample 56 are controlled in accordance with a software program supplied by LABVIEW® Version 5.0.1 Programmable Software available from National Instrument Company of Austin, Tex. Computer means 10 also include conventional means for producing processable data resulting from the scratching of the surface of test sample 56; conventional means for storing the processable data, and means for displaying the processable data in a visual or graphic form, such as on a CRT screen 12 or a graph plotter 12B.

A video system 14 is utilized for capturing deformation occurring on the surface test sample 56 during the experiment, and for conducting analysis of the scratch damage thereafter. Video system 14 is also very useful for positioning of indentor 32, for leveling of test sample 56, and for setting up experiments. Video system 14 is a conventional system, which is preferably connected to a conventional video recording system (not shown) to store the images produced video system 14 during the experiment. Optionally, a microscope (not shown) may be used for viewing the damage to the test coating. Preferably, apparatus 1 is placed inside a thermally insulated chamber (not shown) to maintain all the components of apparatus 1 at a constant temperature, preferably at room temperature. Preferably, series of light sources are strategically positioned inside the insulated chamber for making adjustments to various components of apparatus 1 and for illuminating the tip of indentor 32 and the surface of test sample 56 during video taping of a scratch produced on the surface of test sample 56 during the test.

Figure 4:
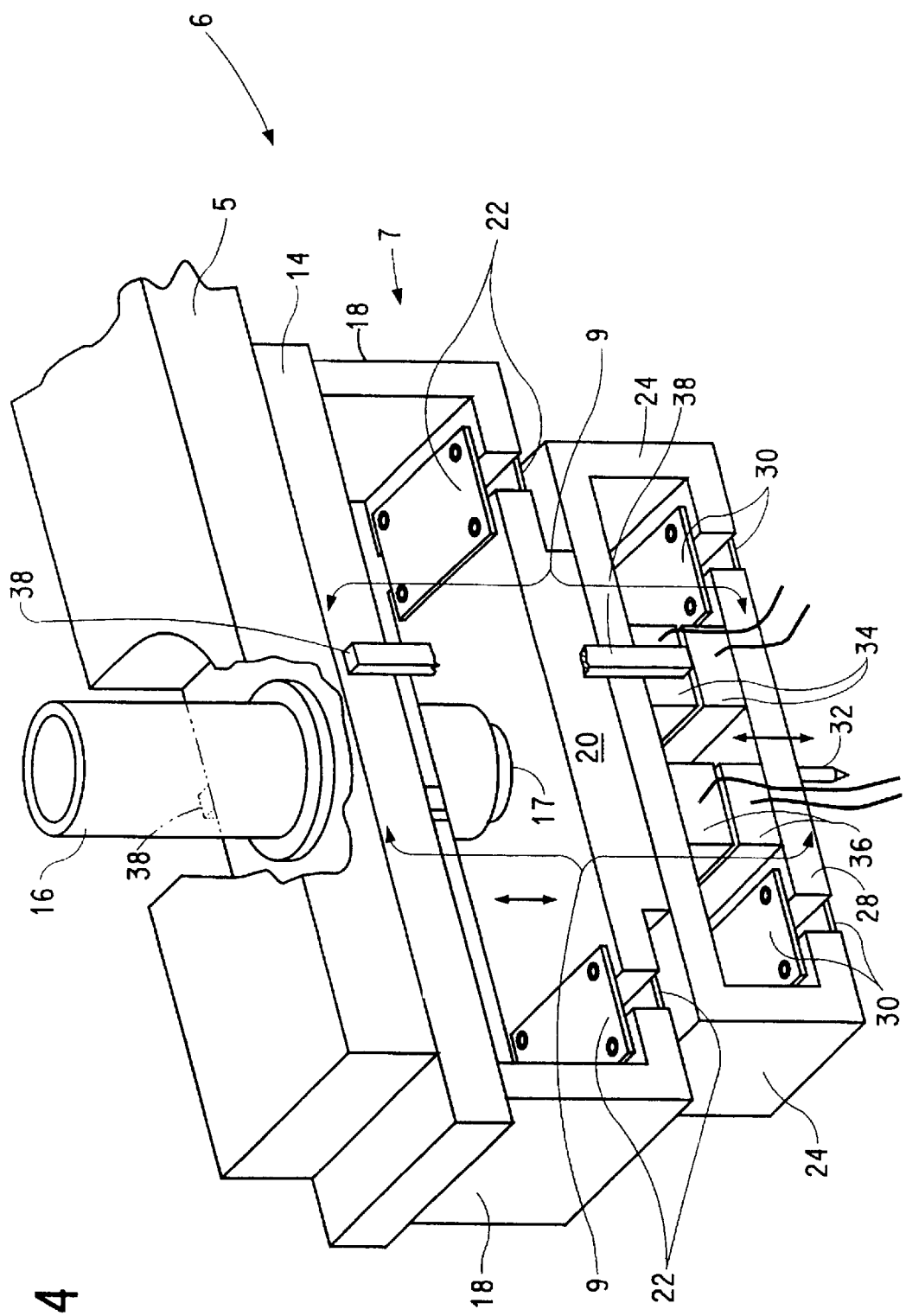
FIG. 4 is a 3-dimensional view of means for indentor guiding of the apparatus of the present invention.
Figure 5:
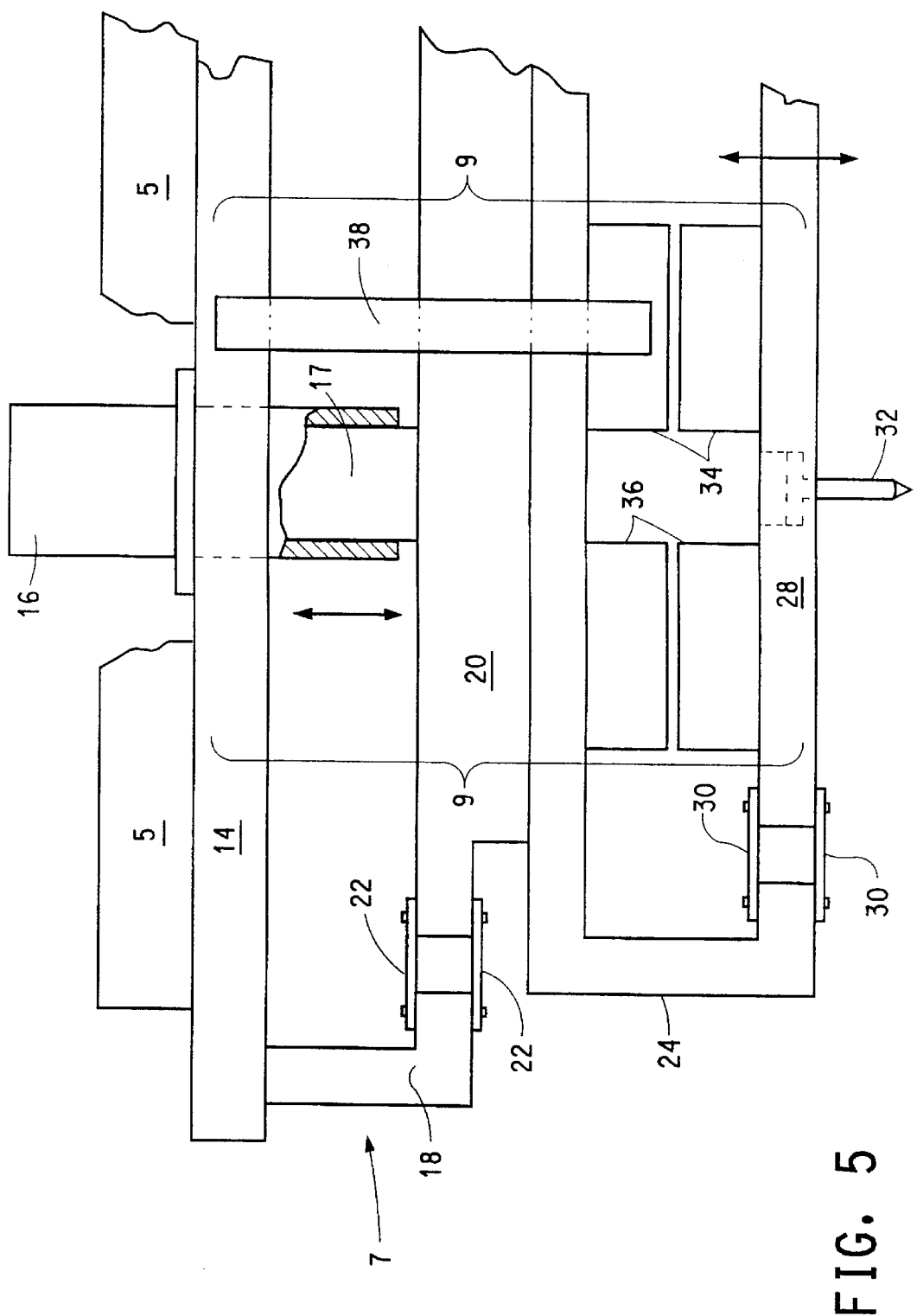
FIG. 5 is an elevational view of the means for indentor guiding of the apparatus of the present invention.

Turning now to more details, FIGS. 4 and 5 show the details of means for indentor guiding 6, which include means 7 for indentor driving having indentor 32 positioned therein and means 9 for sensing travel of indentor 32 towards and away from the surface of test sample 56.

Means 7 for indentor driving includes a stationary bracket 14 affixed to arm 5. Both ends of a movable bracket 20 are connected to stationary bracket 14 through first flexible means 22 connected at bracket ends 18 of stationary bracket 14 so as to provide a single degree of freedom to movable bracket 20. Bracket ends 24 of movable bracket 20 are connected to both ends of an indentor holder 28 through second flexible means 30 to provide a single degree of freedom to indentor holder 28. First flexible means 22 and second flexible means 30 each include a pair of diaphragm springs connected at each bracket end 18 and 24 of stationary bracket 14 and movable bracket 20, respectively. The diaphragm springs are made of nickel-iron alloy, available from Hamilton Precision Metals, Inc. of Lancaster, Pa., which not only has a constant elastic modulus over a large temperature range and a high yield strength, but this alloy also has a lower thermal expansion coefficient compared to other spring materials. The aforedescribed fixed-end double cantilever-beam structure of first flexible means 22 and second flexible means 30 is designed to resist against bending moments and tangential forces such that only a single degree of freedom, generally in a vertical direction, is allowed. Indentor 32 is centrally positioned on indentor plate 28, at equidistance from either end of indentor plate 28 to further ensure that indentor 32 is provided with only one degree of freedom of movement, i.e., no rotational or angular movements. The shape of the tip of indentor 32 may be rounded with a radius in the range of from 1 micron to 10 microns. Alternatively, it may be provided with a pyramidal shape. The tip of indentor 32 is made of diamond, corundum, topaz or quartz. The degree of desired hardness of the tip depends upon the hardness of test sample 56. Diamond tip is preferred. An exemplar of indentor 32 in an indentor available from Synton Company of Lyss, Switzerland, which has a rounded tip with a radius of 3 microns.

Means for indentor driving 7 further include energizing means 16 positioned on stationary plate 14. An actuating core 17 of energizing means 16 is affixed to movable bracket 20, such that when energizing means 16 are energized, movable bracket 20 and indentor plate 28 having indentor 32 positioned therein travel only in a direction perpendicular to the surface of test sampler 56. Energizing means 16 preferably include a low voltage piezo translator (LVPZT) and a controller, which provides the energy to the LVPZT. These LVPZTs elongate when an electrical voltage is applied to them. Thus, one is able to provide an accurate and continuous motion to indentor 32 in a predetermined manner. The total movement of indentor 32 of up to about 90 micrometers with a resolution of 2 nanometers can be obtained by using LVPZT Model Nos. P-840.60 or P-841.60 along with their controllers, available from Physik Instremente, (PI) GmbH & Co, through its subsidiary Polytec PI Inc. of Auburn, Mass., with an operating voltage of up to 120 Volts. The resulting normal force experienced by the surface of test sample 56 is up to 100 milli-newtons with a resolution of 2 micro-newtons.

Means 9 for sensing travel of indentor 32 towards and away from the surface of test sample 56 include first sensing means 34, which measures the penetration of the tip of indentor 32 into test sample 56 and second sensing means 36 for measuring the normal force experienced by test sample 56 when the tip of indentor 32 penetrates into test sample 56. First sensing means 34 and second sensing means 36 respectively generate data on tip penetration and the normal force, which are conveyed to means for conditioning input and output signals 12A of computer means 10. Based on these data, means 12A control the energy supplied to energizing means 16 and the motions of indentor 32 and test sample 56 in accordance with the software program provided through computer means 10.

A stationary first component of first sensing means 34 is mounted on a pair of struts 38 positioned on either side of stationary bracket 14 and movable bracket 20. Struts 38 affixed to stationary bracket 14 allow movable bracket 20 and indentor holder 28 to move freely therewithin. A movable first component of first sensing means 34 is mounted on indentor holder 28, such that when indentor holder 28 travels, the gap between the stationary first component and movable first component of first sensing means 34 varies in accordance with the movement of indentor holder 28, thereby generating an analog output, which is conveyed to means for conditioning input and output signals 37A. Similarly, a stationary second component of second sensing means 36 is mounted on movable bracket 20 and a movable second component of second sensing means 36 is mounted on indentor holder 28, such that when indentor holder 28 travels, the gap between the stationary second component and movable second component of second sensing means 36 varies in accordance with the normal force of experienced by test sample 56, thereby generating an analog output, which is conveyed to means for conditioning input and output signals 12A. First sensing means 34 and second sensing means 36 may be same, such as for example, Model D-050-00 capacitive sensor available from Physik Instremente,(PI) GmbH & Co, through its subsidiary Polytec PI Inc. of Auburn, Mass.

Figure 6:
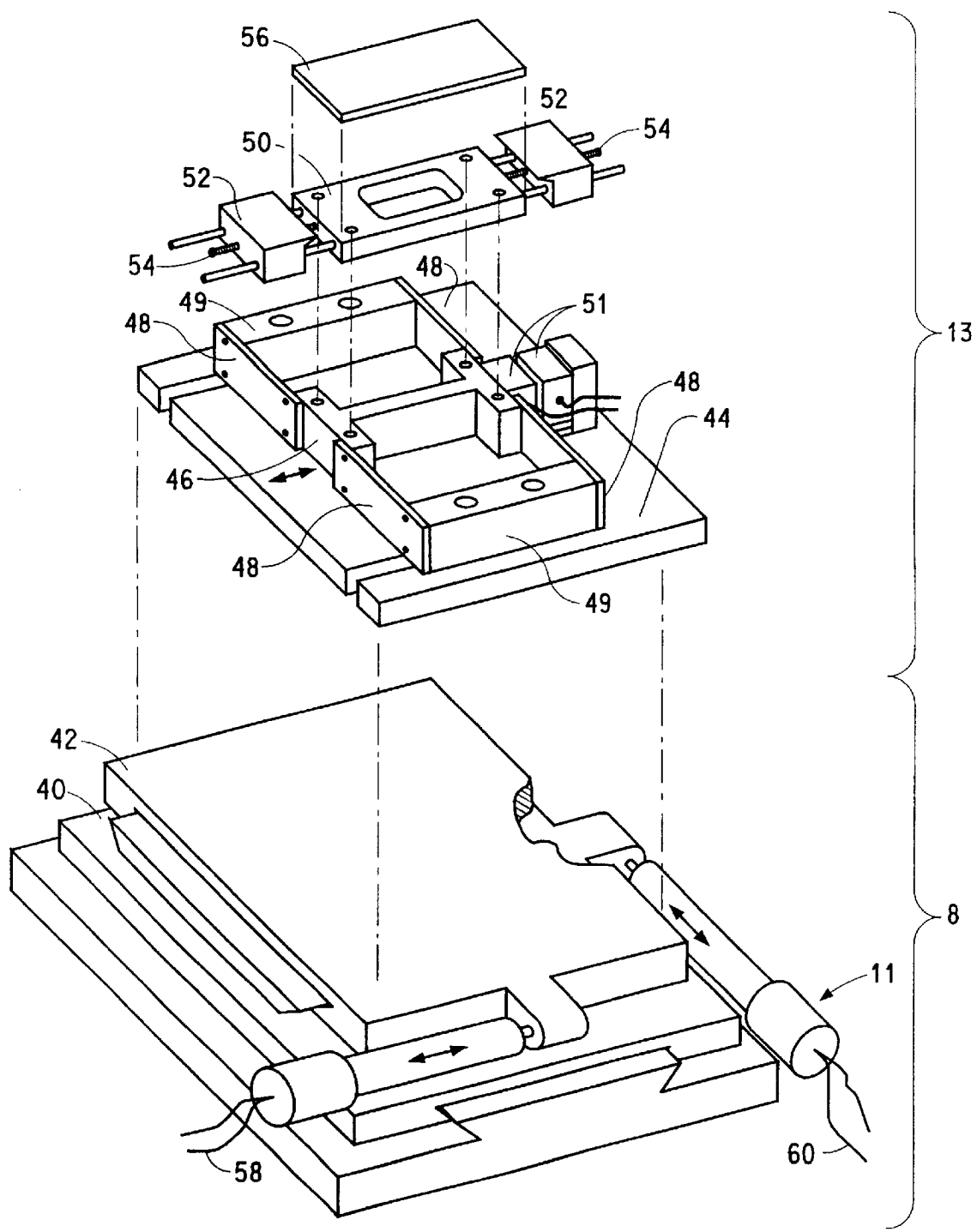
FIG. 6 is a 3-dimensional exploded view of means for directing test sample of the apparatus of the present invention.
Figure 7:
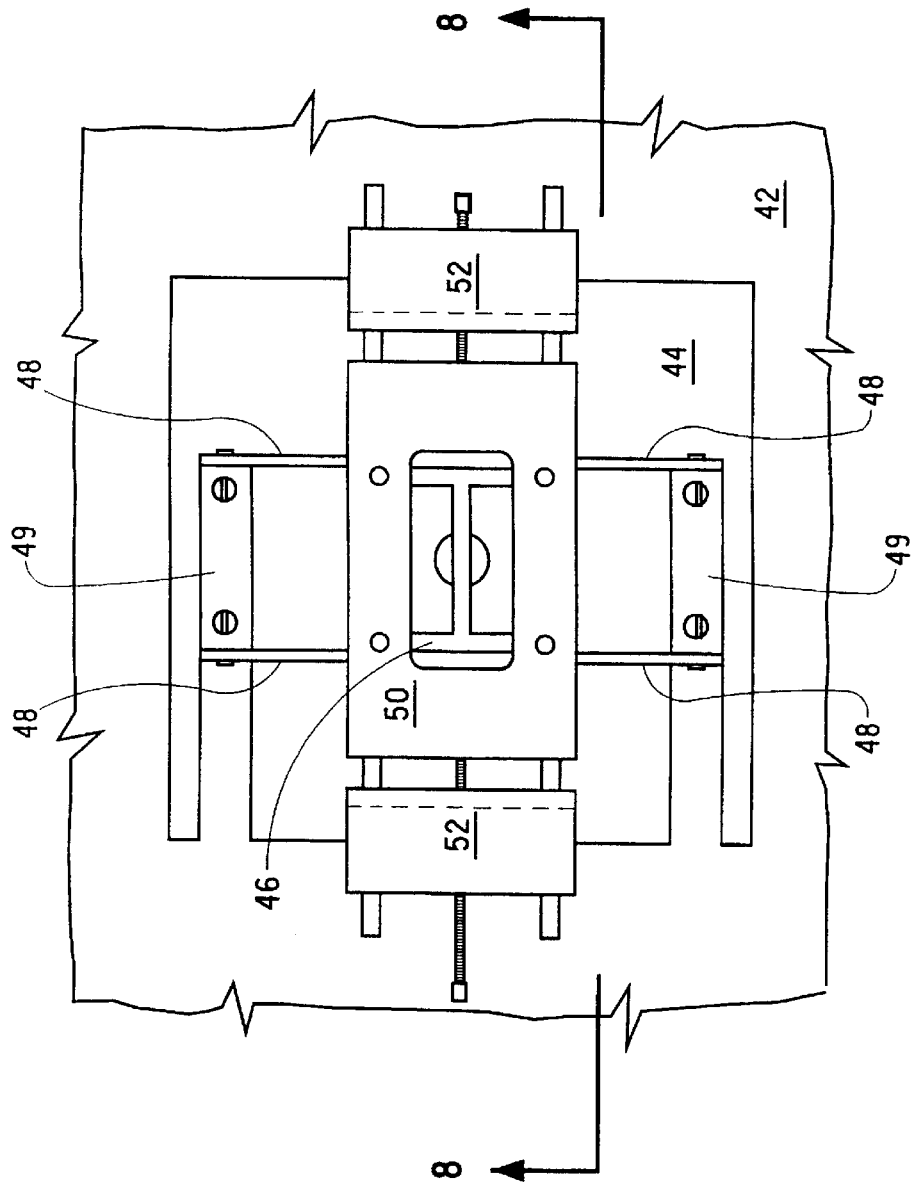
FIG. 7 is a plan view of holder means and a portion staging means of the means for directing test sample of the apparatus of the present invention.
Figure 8:
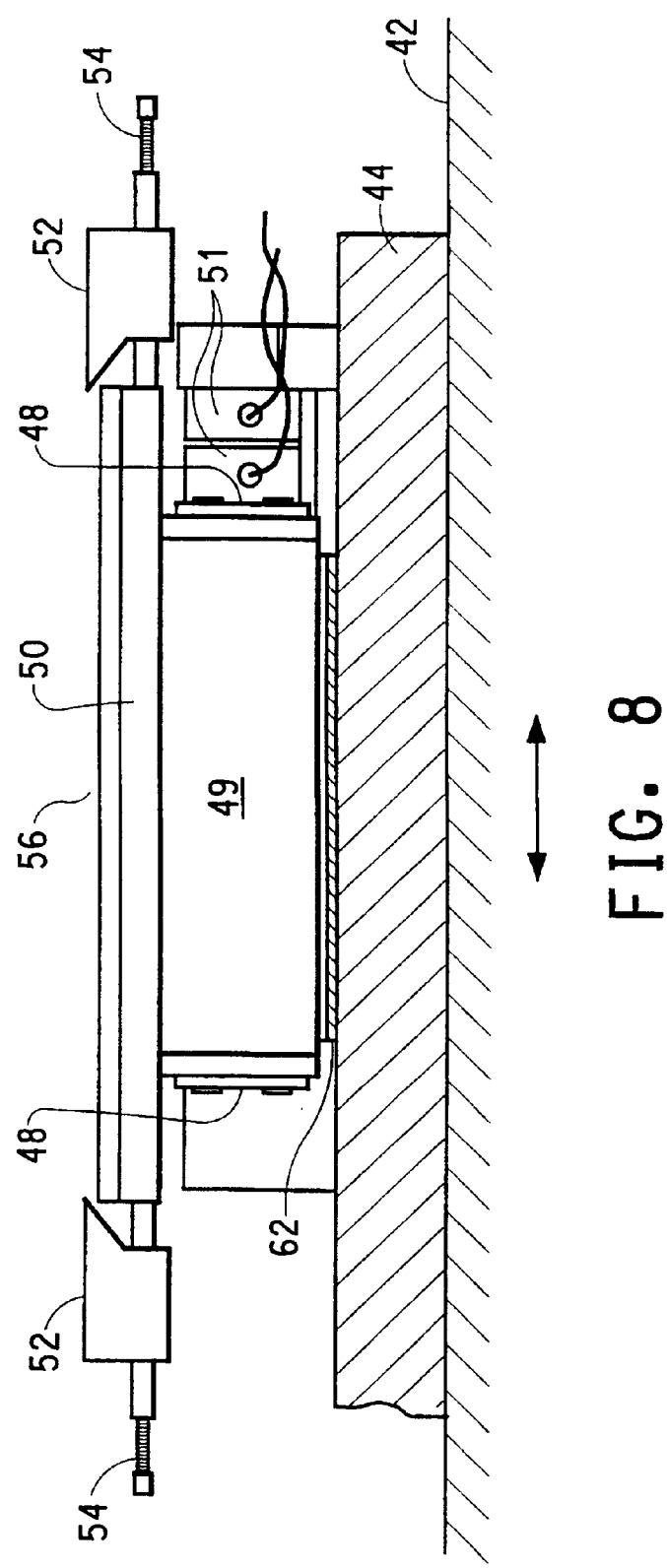
FIG. 8 is a side view taken along the section line 8—8 of FIG. 7.

FIGS. 6, 7 and 8 provide details of means 8 for directing test sample. FIG. 6 provides details of staging means 11 for traversing test sample 56 in a direction tangential to indentor 32, such that when the tip of indentor 32 is simultaneously driven into test sample 56, a scratch is produced on the surface of test sample 56. FIGS. 6, 7 and 8 provide details of holder means 13 that secure test sample 56 thereon with its exposed surface in perpendicular relationship with indentor 32.

As seen in FIG. 6, staging means 11 include a first staging block 40 affixed to base 2 of apparatus 1 and a second staging block 42 affixed stop first staging block 40, such that holder means 13 affixed atop second staging block 42 can be moved and accurately positioned along the x and y axis. Upon input signals from computer means 10, driving means 60 for first staging block 40 and driving means 58 for second staging block 42 provide motion along the X and Y axis to holder means 13 affixed atop second staging block 42. One of the suitable staging systems is the Nanomover™ System available from Melles Griot, Irvine, Calif. These micropositioners have a resolution of 50 nanometers with absolute accuracy of ±1 micron and a total range of travel of 25 mm.

As seen in FIGS. 6, 7 and 8 holder means 13 include a sample holder support block 44 secured atop second staging block 42. If desired, a dampening film 62 of a silicone compound may be provided between sample holder support block 42 and second staging block 42 to further reduce transmission of any high frequency noise from second staging block 42 to sample holder support block 44. Preferably, a pair of conventional single axis-tilt platforms (not shown) positioned at 90° to one another are provided between sample holder support block 44 and second staging block 42 to facilitate leveling of test sample 56 secured in holder means 13. For example, single-axis tilt platforms (Model No. TGN 80) available from Newport Company of Irvine, Calif. are well suited for this purpose. These platforms have a travel range of ±2.5° with a resolution of 20 arcsec and sensitivity of 2 arcsec.

A pair of wedge blocks 49 are secured to sample holder support block 44 and an 'I'-block 46 is connected to wedge blocks 49 through third flexing means 48 connected to legs of 'I'-block 46 for providing a single degree of freedom to 'I'-block 46 along the direction shown. Third flexible means 48 each include a pair of diaphragm springs connected on each side of wedge block and each leg of 'I'-block 46. The diaphragm springs are made of nickel-iron alloy, available from Hamilton Precision Metals, Inc. of Lancaster, Pa. 'I'-block 46 is positioned above the surface of sample holder support block 44 to allow free back and forth movement along the arrow shown. A sample holder 50 is affixed stop 'I'-block 46. Sample holder 50 is provided with a pair of sample holder clamps 52, which ride over a pair of mounting rods. Each sample holder clamp 52 is provided with a clamping screw 54, such that test sample 56 can be secured by tightening holder clamps 52 around test sample 56 by means of clamping screws 54.

Apparatus 1 further includes third sensing means 51 for measuring tangential force experienced by test sample 56 during the scratching of the test sample by the tip of indentor 32 at it traverses across the surface of test sample 56. A stationary third component of third sensing means 51 is mounted on sample holder support block 44 and a movable third component of third sensing means 51 is mounted on the side of 'I'-block 46, such that when indentor 32 scratches the surface of test sample 56, the gap between the stationary third component and movable third component of third sensing means 51 varies in accordance with the tangential force experienced by test sample 56. An analog output resulting therefrom is then conveyed to means for conditioning input and output signals 12A. Third sensing means 51 may be the same as first sensing means 34 or second sensing means 36, such as for example, Model D-050-00 capacitive sensor available from Physik Instremente,(PI) GmbH & Co, through its subsidiary Polytec PI Inc. of Auburn, Mass.

Depending on the size of the diaphragm springs in first flexing means 22, second flexing means 30 and third sensing means 51, and the power of energizing means 16, test apparatus 1 can be modified to provide apparatus I with different degrees of testing capabilities and resolutions, suitable for various test applications. Apparatus 1 is capable of producing micro-scratches on coatings or films having a thickness in the range of 1 to 1000 microns for measuring their mar resistance. In carrying out such tests, test sample 56 is secured in sample holder 50. Test sample 56 is then initially leveled by using bubble level and preferably with single-axis tilt platforms to substantially level the exposed surface of test sample 56 by scanning the surface of test sample 56. By using adjustable arm 5 indentor 56 is positioned close to test sample 56 and by using video system 14 the tip of indentor 32 is brought close to within 5 microns of the exposed surface of test sample 56, which occurs when the indentor tip and its reflection substantially touch one another. Final adjustments are generally made by using the travel provided by energizing means 16, which when energized, pushes movable bracket 20 that in turn pushes indentor holder 28 having indentor 32 thereon to contact the exposed surface of test sample 56. When such contact occurs, second sensing means 36 provide the normal force experienced by the surface of test sample 56. The normal force is adjusted to a constant normal force insufficient to produce any significant damage the underlying surface of test surface 56. Typically such a normal force is around 20 micro-newton ($\mu$N) for resinous coatings.

First, the surface of test sample 56, to be scratched, is profiled by scanning the tip of indentor 32 in a set direction over the surface at a set speed provided by powering staging means 11 through a set distance, typically of 3 mms, and setting the normal force with which the tip of indicator 32 touches the surface of test sample 56 at a profile level sufficient to determine its contour without altering or damaging the surface, i.e., at a normal force of 20 micro-newtons ($\mu$N). The normal force is maintained at the profile level during the profiling of the surface by utilizing a continuos fed back from a closed-loop control system provided by staging means 11 and computer means 10. The resulting data is stored as pre-scratch profile data in the memory means of computer means 10.

A ramp scratch is then performed by driving the tip of indentor 32 at a set rate into the surface of test sample 56 while simultaneously traversing the surface of test sample 56 at a speed provided staging means 11 in the same set direction through the same set distance, by referencing the stored pre-scratch profile data. Thus, by utilizing the pre-scratch data during the ramp scratching of the surface of test sample 56, any errors that may be contributed by the surface variation, i.e., hills and valleys, of test sample 56 are eliminated. As a result the tip of indentor produces a scratch of desired depth that is unaffected by the surface variations of test sample 56. The resulting signals are stored as tip-displacement profile data in the memory means of computer means 10. Generally, during the ramp scratch, the normal force experienced by the surface of test sample 56 starts at 0. Then after a five second delay, while test sample 56 continues to move, the normal force is steadily increased at a rate of 0.02 milli-newtons per seconds to a defined maximum. If desired, the rate may be increased in steps or it may be maintained at a constant level.

Finally, the surface of the scratch is profiled by scanning it with the tip of indentor 32 at a set speed provided by powering staging means 11 through the same set distance at the same profile level normal force, i.e., a normal force of 20 $\mu$N, in the same set direction established during the pre-scratch profiling of the surface. The normal force is maintained at the profile level during the profiling of the scratch by utilizing a continuous feed back from a closed-loop control system provided by staging means 11 and computer means 10. The resulting signals are stored as post-scratch profile data in the memory means of computer means 10. The pre-scratch, tip-displacement and post-scratch-profile data are processed into processable data, which may be then displayed in a visual or graphic form on displaying means 12 to determine the mar resistance of test sample 56.

In addition, the normal force experienced by test sample 56, as the tip is driven into test sample 56, is measured and stored as normal force profile data. The tangential force experienced by test sample 56 during the scratching of test sample 56 is also measured and stored as tangential force profile data. The normal and tangential force profile data are integrated into the processable data.

Figure 9:
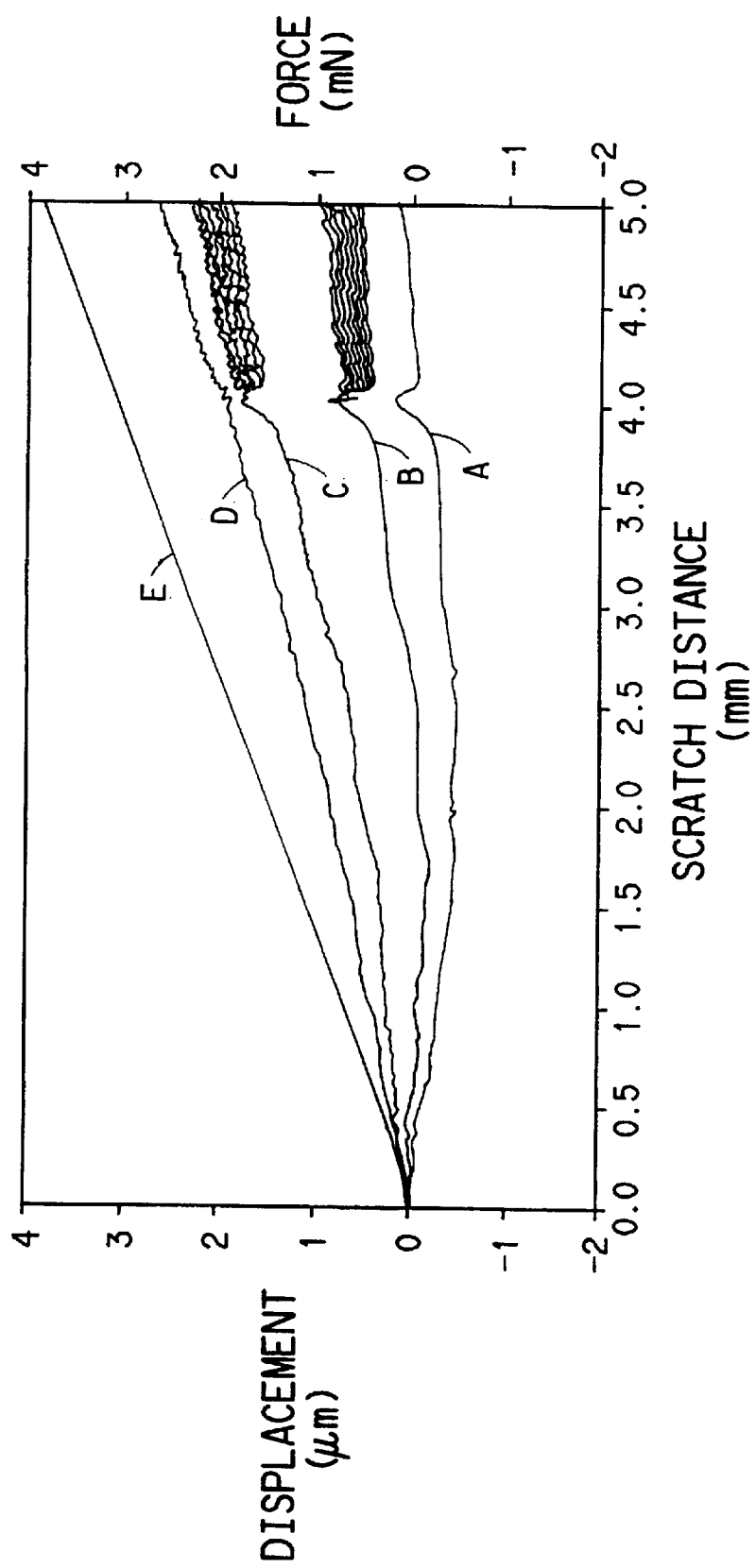
FIGS. 9, 10 and 11 are graphs showing the results of a typical micro-scratch experiment obtained by using the apparatus of the present invention.

Test sample 56 tested by using the method of and apparatus 1 of the present invention included various coatings. FIG. 9 shows the results of a micro-scratch experiment obtained on a top clear coat having a thickness of ~30 $\mu$m that was made from a styrenated-acrylic/melamine composition applied over a black basecoat. Indentor 32 with a diamond tip having a 1 $\mu$m was used.

Figure 10:
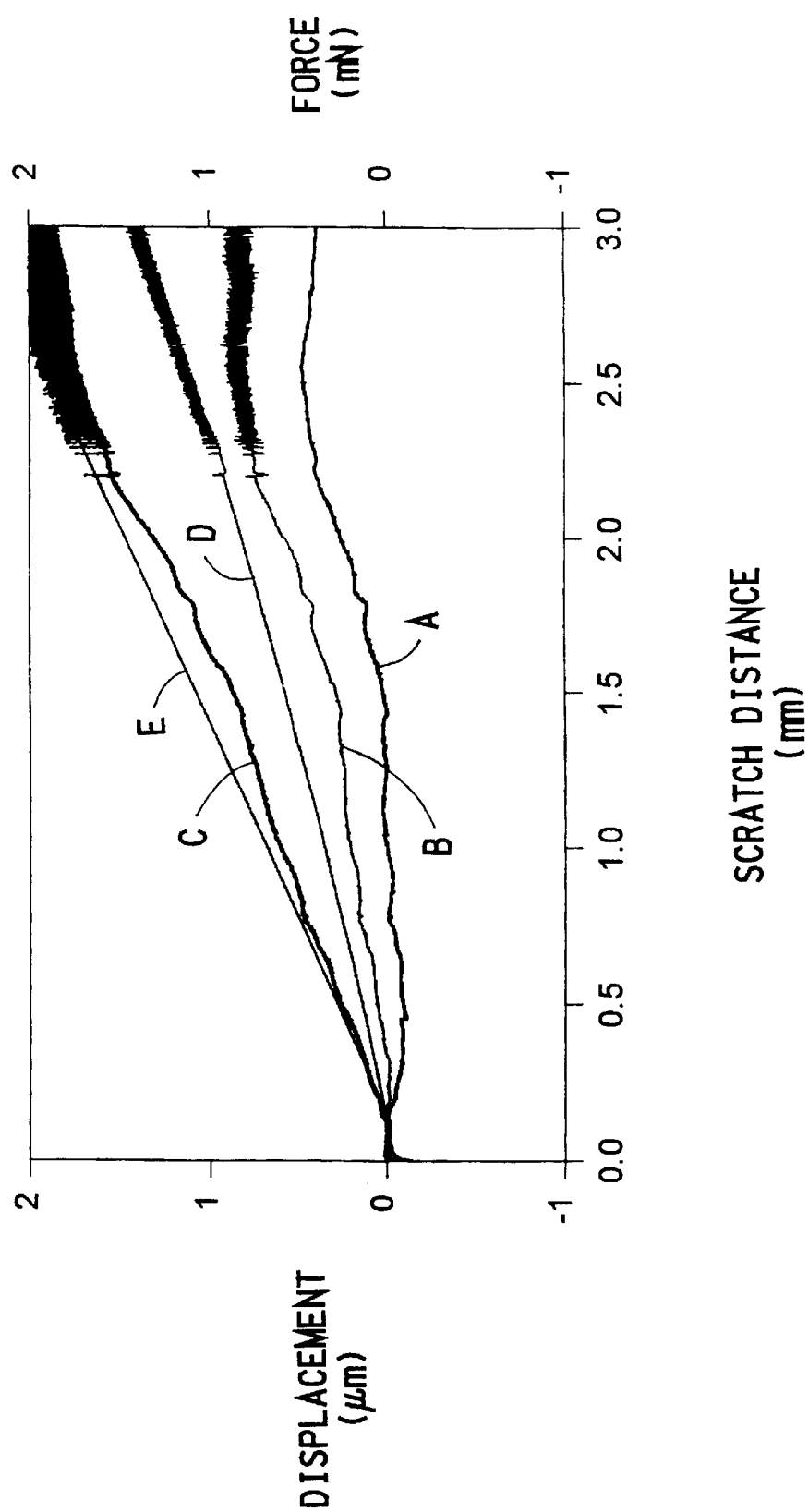
Figure 11:
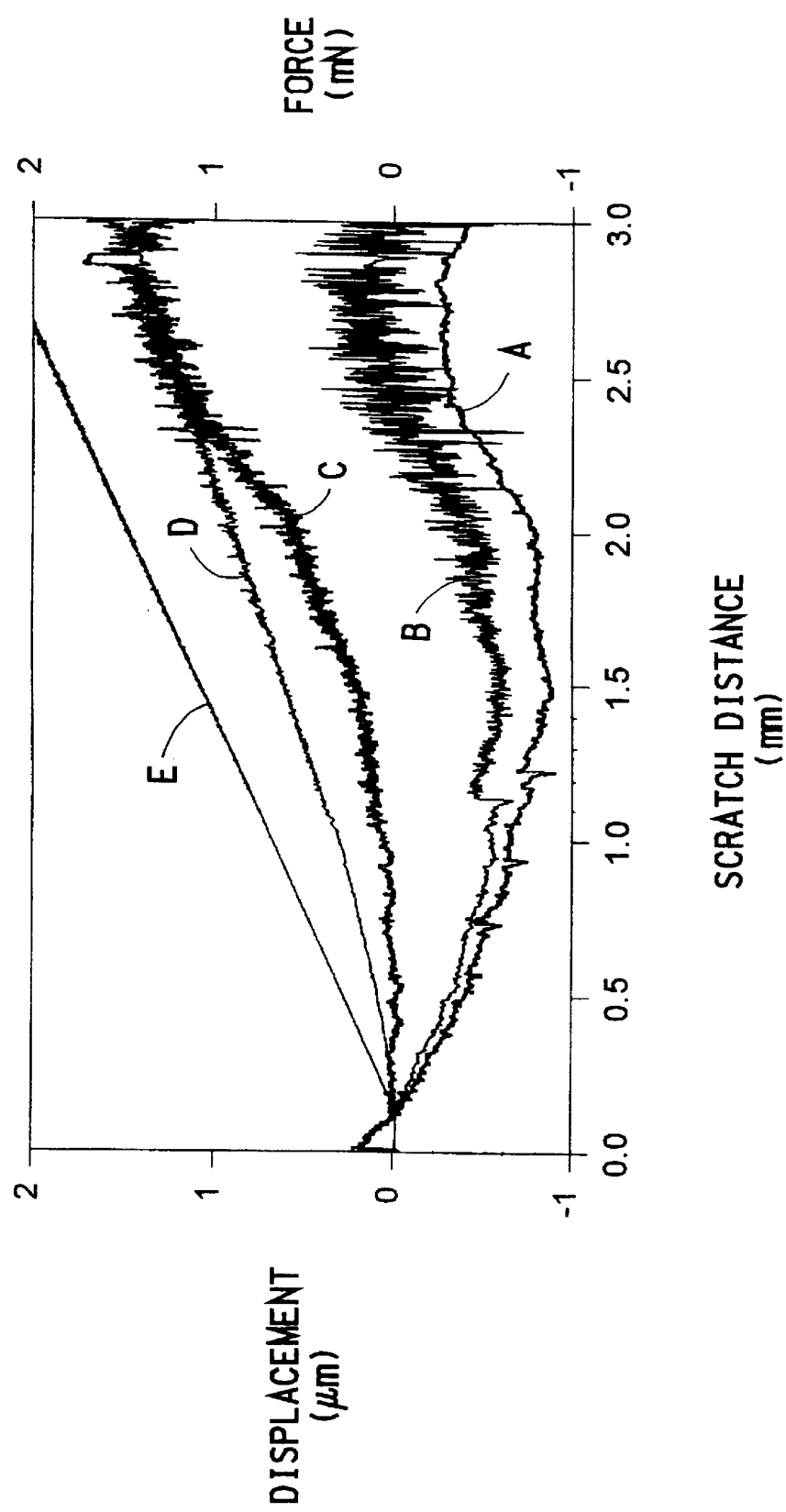

FIGS. 10 and 11 show the result of a micro-scratch experiment obtained by using two different clear coating compositions.

Trace A in the graphs of FIGS. 9, 10 and 11 represents the pre-scratch profile of an undamaged surface of test sample 56, trace D represents the tip-displacement profile of the tip of indentor 32 as it penetrates into test sample 56 over the set distance, trace B represents the post-scratch profile of the scratch. As seen from trace D and trace B, the coating makes a significant recovery after scratching of the surface. Traces E and D are profiles of normal force and tangential force experienced by test sample 56 during the experiment. The damage to coating is obtained by subtracting the pre-scratch profile depth of trace A from post-scratch profile depth of trace B.

In the early region of the scratch, traces A and B are superimposed, signifying that the deformation of coating is totally recovered, i.e., the deformation was elastic. As the load increased the two traces start diverging, signifying the beginning of visco-plastic deformation, a magnified version can be seen in FIG. 1. The amount deformation increased smoothly as the normal force was increased. At a distance of about 4.1 mm in FIG. 9 (normal force of 3 mN) and about 2.15 mm (normal force of 1.8 mN) in FIG. 10, the character of the trace B underwent an abrupt change. The tangential force as shown by trace D profile and tip-displacement profile as shown by trace C started to rapidly fluctuate indicating that a fracture had occurred, a magnified version can be seen in FIG. 2. As the normal load increased further, both the frequency and magnitude of the rupture increased and eventually debris was generated. By comparison to FIGS. 9 and 10, the test data of a coating represented in FIG. 11, indicates that the coating represented in FIG. 11 would have less mar resistance, since the fracture state occurred quite early as the micro-scratch was produced. Additionally, the longer the period during which coating stays in the elastic or visco-plastic zones and the closer trace B follows trace A, the better will be the mar resistance of coating.

The present invention may be also used for comparing mar resistance of various surfaces by penetrating indentor 32 to a uniform set depth, at a set speed and set normal force and then comparing micro-scratches produced on various surfaces. Alternatively, the apparatus of the present invention may be used to determine the surface roughness of coatings or films, hardness of films or coatings, such as by profiling the surface of a test sample or to measure the uniformity of thickness of coatings or films by penetrating the indentor tip through the entire thickness of the film.

The present invention is well suited for measuring mar resistance of various types of coatings, such as clear and pigmented coatings used as automotive, maintenance, wood, plastic or paper coatings; scratch-resistant coatings applied over eyeglass (spectacles) lenses; antireflective and antiglare coatings applied over camera and binocular lenses; various metallic coatings, such as electroplating, chrome and titanium dioxide (TIN) coatings on metal substrates and electroless nickel, copper, silver and gold coatings applied over metal substrates.

What is claimed is:

1. An apparatus (1) for measuring mar resistance of a test sample (56) comprising:
    means for indentor guiding (6), said means being mounted on a post (4) of said apparatus (1) comprises:
    means for indentor driving (7) having an indentor (32) positioned therein, and means for sensing travel (9) of said indentor towards and away from a surface of said test sample; and
    means for directing said test sample, said means being positioned on a base (2) of said apparatus comprising:
    holder means (13) to secure said test sample (56) thereon with the surface of said test sample (56) in perpendicular relationship with said indentor (32), and staging means (11) for traversing said test sample in a direction tangential to said indentor, such that when a tip of said indentor (32) is simultaneously driven into said test sample, a scratch is produced on the surface of said test sample.

2. The apparatus of claim 1 wherein said means for indentor driving comprise:
    a stationary bracket (14) affixed to an arm (5) of said post (4);
    energizing means (16) affixed to said stationary bracket (14) for providing movement to a movable bracket (20) flexibly connected to said stationary bracket (14) through first flexing means (22) which provide a single degree of freedom to said movable bracket (20); and
    an indentor holder (28) flexibly connected to said movable bracket (20) through second flexing means (30) which provide a single degree of freedom to said indentor holder (28), such that when said energizing means (16) are energized, said movable bracket (20) and said indentor holder (28) having said indentor (32) positioned therein travel only in a direction perpendicular to the surface of said test sample (56).

3. The apparatus of claim 2 wherein said energizing means (16) comprise a low voltage piezo translator.

4. The apparatus of claim 2 wherein said first (22) and second (30) flexing means each comprise a pair of diaphragm springs.

5. The apparatus of claim 2 wherein said first flexing (22) means comprises a pair of diaphragm springs connected at both ends of said movable (20) and said stationary brackets (14).

6. The apparatus of claim 2 wherein said second flexing means (30) comprise a pair of diaphragm springs connected at both ends of said indentor holder (28) and said movable bracket (20).

7. The apparatus of claim 2 wherein said first flexing means (22) comprise three pairs of diaphragm springs connected radially at three locations on said movable (20) and said stationary brackets (14), such that each pair of said diaphragm springs is 120° apart from the other.

8. The apparatus of claim 1 wherein said means for sensing travel (9) of said indentor (32) comprise:
    first sensing means (34) for measuring penetration of said indentor (32) into said test sample (56); and
    second sensing means (34) for measuring normal force experienced by said test sample (56) when said indentor (32) penetrates into said test sample (56).

9. The apparatus of claim 8 wherein said first sensing means (34) comprise a stationary first sensing component mounted on a strut (38) affixed to a stationary bracket (14) and a movable second sensing component affixed to said indentor holder (28).

10. The apparatus of claim 9 wherein said stationary first sensing component and said movable first sensing component form a pair of capacitive sensors.

11. The apparatus of claim 8 wherein said second sensing means (36) comprise a stationary second sensing component affixed to a movable bracket (20) and a movable second sensing component affixed to an indentor holder (28).

12. The apparatus of claim 11 wherein said stationary second sensing component and said movable second sensing component form a pair of capacitive sensors.

13. The apparatus of claim 8 wherein said means for directing said test sample further comprises third sensing means for measuring tangential force (51) experienced by said test sample (56) during scratching of said test sample by said indentor.

14. The apparatus of claim 1 or 13 further comprising computer means (10) which comprise:
    means for conditioning input and output signals (12A) to and from said means for indentor guiding (6) and said means for directing said test sample to control motion of said indentor (32) and said test sample (56) in accordance with a software program;
    means for producing data resulting from the scratching of the surface of said test sample;
    means for storing said data; and
    means for displaying said data in a visual or graphic form.

15. The apparatus of claim 14 wherein said data comprise:
    pre-scratch profile data which results when said tip is traversed along the surface of said test sample before the surface is scratched by said tip;
    tip-displacement profile data which results when said tip is driven into said test sample;
    post-scratch profile data which results when said tip is traversed along the scratch; and
    normal force profile data which results when said tip is driven into said test sample.

16. The apparatus of claim 15 wherein said data further comprise tangential force profile data which results during scratching of said test sample.

17. The apparatus of claim 1 wherein said tip of said indentor (32) is diamond.

18. The apparatus of claim 1 wherein said test sample (56) is a clear coating applied over an automotive body.

19. The apparatus of claim 1 wherein said tip of said indentor (32) is corundum.

20. The apparatus of claim 1 wherein said tip of said indentor (32) is topaz.

21. The apparatus of claim 1 wherein said tip of said indentor (32) is quartz.

22. The apparatus of claim 1 wherein said test sample (56) is an applied clear coating.

23. The apparatus of claim 1 wherein said test sample (56) is a clear coating applied over prescription glasses.

24. The apparatus of claim 1 wherein said test sample (56) is a clear coating applied over lenses.

25. The apparatus of claim 1 wherein said test sample (56) is a clear coating applied over wood substrate.

26. The apparatus of claim 1 wherein said test sample (56) is a clear coating applied over plastic substrate.

27. The apparatus of claim 1 wherein said test sample (56) is a clear coating applied over a paper substrate.

28. A method of measuring mar resistance of a test sample (56) comprising:

securing said test sample (56) in staging means (11) of an apparatus (1);

positioning an indentor (32) in a perpendicular relationship to an exposed surface of said test sample (56), such that a tip of said indentor (32) is in contact with said surface of said test sample (56); and driving said tip of said indentor (32) into the surface of said test sample (56) at a set rate while simultaneously traversing said test sample (56) in a direction tangential to said indentor (32) at a set speed in a set direction for scratching said surface of said test sample (56) to produce a scratch thereon.

29. The method of claim 28 further comprising:

producing signals in response to said scratching of said test sample (56) and converting said signals into data; and displaying said data in a visual or graphic form.

30. A method of measuring mar resistance of a test sample (56) comprising:

securing said test sample (56) in staging means (11) of an apparatus (1);

positioning an indentor (32) in a perpendicular relationship to the exposed surface of said test sample (56), such that a tip of said indentor (32) is in contact with said surface of said test sample (56);

profiling the surface of said test sample (56) for a set distance by traversing said tip over said test sample (56) in a direction tangential to said indentor (32) in a set direction and storing pre-scratch profile data resulting therefrom;

driving said tip of said indentor (32) into the surface of said test sample (56) at a set rate while simultaneously traversing said test sample (56) in a direction tangential to said indentor (32) at a set speed in said set direction for said set distance obtained by referencing said pre-scratch profile data to produce a scratch on said surface of said test sample (56), and storing tip-displacement profile data resulting therefrom;

profiling the scratch on the surface of said test sample (56) by traversing said tip over the scratch in a direction tangential to said indentor (32) in said set direction for said set distance and storing post-scratch profile data resulting therefrom;

processing said pre-scratch, said tip-displacement and said post-scratch profile data; and displaying the processed data in a visual or graphic form.

31. The method of claim 30 wherein said step of profiling the surface and said step of profiling the scratch on the surface comprises:

setting a normal force with which said tip touches the surface or scratch at a profile level sufficient to determine its contour without altering the surface or scratch; and maintaining said normal force at said profile level during said step of profiling the surface and said step of profiling the scratch on the surface by utilizing a continuous feed back from a closed-loop control system.

32. The method of claim 30 further comprising:

measuring normal force experienced by said test sample (56) as said tip is driven into said test sample (56) and storing normal force profile data resulting therefrom;

measuring tangential force experienced by said test sample (56) during said scratching of said test sample (56) and storing tangential force profile data resulting therefrom; and integrating said normal force profile data and said tangential force profile data within said processed data.

* * * * *